United States Patent [19]

Sager et al.

[11] Patent Number: 5,154,921
[45] Date of Patent: Oct. 13, 1992

[54] PROMOTION OF MATURATION OF HEMATOPOIETIC PROGENITOR CELLS

[75] Inventors: Ruth Sager, Brookline, Mass.; Douglas Trask, Miami, Fla.; Phong Le, Durham, N.C.

[73] Assignee: Dana-Farber Cancer Institute, Inc., Boston, Mass.

[21] Appl. No.: 552,746

[22] Filed: Jul. 13, 1990

[51] Int. Cl.$^5$ .................. A61K 35/28; C12N 5/06; C12N 5/08; C07K 13/00

[52] U.S. Cl. .............. 424/93 U; 435/240.21; 435/240.2; 530/350; 530/351; 424/93 V; 424/93 W; 424/93 AA

[58] Field of Search .............. 530/351; 435/240.1, 435/240.3, 240.21; 424/85.1, 534, 93; 604/4

[56] References Cited

U.S. PATENT DOCUMENTS 4,877,729 10/1989 Clark et al. .................. 435/69.5

FOREIGN PATENT DOCUMENTS 0211684 8/1986 European Pat. Off. .

OTHER PUBLICATIONS

Anisowicz et al., 84 Proc. Natl. Acad. Sci., 7188-7192, 1987.
Anisowicz et al., 85 Proc. Natl. Acad. Sci., 9645-9649, 1988.
Bardoni et al., Proceedings Am. Assn. Cancer Res., 30:419, No. 1664, 1989.
PCT Search Report issue in application PCT/US91/04885 dated Oct. 28, 1991.
Hopp et al., Biotechnology, vol. 6, pp. 1204-1210, 1988.
Richmond et al., Cancer Research, 43:2106-2115, 1983.
Richmond et al., J. Cell Biochem. Suppl., 11A, p. 38, 1987.
Richmond et al., The EMBO Journal, vol. 7, No. 7, pp. 2025-2033, 1988.
Richmond & Thomas, J. Cell Biol., 107:40a, No. 203, 1988 (abstract).
Jandl, Blood, pp. 441-450, Little, Brown, Boston, 1987.
Wen et al., The EMBO Journal, 8:1761-1766, 1989.
Schroder et al., J. Exp. Med., 171:1091-1100, Apr. 1990.

Primary Examiner—John J. Doll
Assistant Examiner—George C. Elliott
Attorney, Agent, or Firm—Janis K. Fraser

[57] ABSTRACT

A method for promoting maturation of a hematopoietic precursor cell of an animal, which method includes the step of contacting the cell with a maturation-promoting amount of GRO, a polypeptide growth factor.

13 Claims, 6 Drawing Sheets

```
GROα  CCAGAAGGGAGGAGAAGCTCACTGG........TGGCTGTGTTCCTGAA..GGAGGCCCCTGCCCTTATAGGAACACAGAAGAGAAGAGAGA....CACAGC
   β  CCAGAAGGAGGAGGAGAAGCTTATTGG........TGGCTGTGTTCCTGAA..GGAGGCCCCTG.CCTTACAGGAACACAGAAGAGAAGAGAGA....CACAGC
   γ  CAGGAGAGAAGTAAGAAGCTTATCAGCGTATCATTGACACTTCCTGCAGGTGCTCCCTGCCCTTACCCAGAGCTGAAAATGAAAAGAACAGCAGCTT

GROα  TGCAGAGCCCACCTGGATTGTGCCTAATGTGTTTGAGCATCGCTTAGGAGAGAAGTCTTCTATTTATTTATTTATTCA........TTAGTTTTGAAGATT
   β  TGCAGAGCCCACCTGGCTTGCGCCTAATGTGTTTCAGCAT.ACTTAGGAGAAGTCTTCTATTTATTTATTTATTTATTTGTTTTAGAAGATT
   γ  TCTAGGCACAGCTGGAAAGGACTTAAGTGTGTTTGACTA...TTTCTTACGAGGTTCTACTTATTTATGTATTTATT.........TTTGAAAGCTT

GROα  CTATGTTAATATTTAGGTGTAAAATAATTAAGGGTATGATTAACTCTACCTCCACACTCTCCTATTATATATTCATTCTTTTTGAAATGTCAACCCAAGT
   β  CTATGTTAATATTTAGGTGTAAAA.....AAGGTTATGATTGAATCTACTACTTCCACACTCTCCATTATATATTTATTGTTTATTTTAGTCAAACCAAGT
   γ  GTATTTTAATATATTTTACATG.CTGTTATTTAAAAGATATGAGTGTGTTCATCAAAGATAGCTCAGTCCTGATTATT.TAATTGGAATATGATGGTTTTA

GROα  TAGTTCAATCTGATTCATATTTAATTTGAAGTAGAATGTTTTCAAATGTTCTCCAGTCATTATGTTAATATTTCTGAG.GAGCCTGCAACATGCCAGC
   β  TAGTTCAATCCTGATTCATATTTAATTTGAACATAGAAGGTTTGCAGATATTCTCAGTCATT.TGTTAATATTTCTTCGTGATGACATATCACATGTCA
   γ  AATGTGTCATTAAAGTAATAATATTTAGTGGGAGACCATAAATGTGT..........CAGCCACCTTGATAA.............ATGACAGGGTGGGAAC

GROα  CACTGTCATAGAGGCTCCCGATCCAAGCAAATGAGAATCATTGTGAAGGCAGGGAATGTATCTGCACATCTGTTTTGTAACTGTTT.......
   β  GCCAGTGTCATACAGGCTCAGGAATCCAAGAAATGCCAGTAAGATCAATGTGACGGACAGGAATCAATGTATGTGTCTATTTT..GTAACTGT....A
   γ  TCCACCCTNGGGGATTCAAATGCAAGT.....AGTGGATCACTGTTAGGTAAGGAATGTATGTACACATCTATTTTTTTATACTTTTTTTTTA

GROα  AGATGAATGTCAGTTGTTATTTATTTATTGAAATGATTTCACAGTGCTGTGGTCAACATTTCTCATGTTGAAACTTAAGAACTAAAATGTTCTAAATATCCCT
   β  AAGATGAATGTCAGTTGTTGTTATTTATTTGAAATGATTTCACAGTGCTGTGGTCAACATTTCTCACATGTTGAAGCTTTAAGAACTAAAATGTTCTAAATATCCCT
   γ  AAAAAGAATGTCAGTTGTTATTTATTTATTCAATTTCAAATATCTCAACATGTTCAACATTTTATGCT..............CAAGTTTCCCT

GROα  TGGACATTTTATGTCTTCTTGTAAGGCATACTGCCTTGTTGTTTAATGGTAGTTTTTACAGTGTTTC........TGGCTTAGAACAAAGGGGCTTAATTAT
   β  TCG.CATTTTATGTCTTTCTTGTAAG...ATACTGCCTTTAATGTTTTAATTATGCAGTGTTTTAATGTTAATTATGCAGTGTTTTC.TATTTAT
   γ  TACACATTTTATGTCTGTGTAGGCATAATGCCTTGTTTTAATGTCCATTCTGCAGCGTTTCTCTTGTCTTCCCTTGGAAAAGAGAATTTATCATTACTGTT

GROα  TGAATGTTTT...CGGagaatataaaataaagcacttatag
   β  TGATGTTTTCAACAAGAACAGGAAAATAAAATATTAAAAATAT
   γ  ACATTTGT...ACAAATGACATGATAATAAAGTTTTATG
```

FIG. 3a

```
                                                        10        20        30
HUMAN GRO:                               CTCGCCAGC----TCTTCCGCTCCTCTCACAGCC
                                         |||||    | | |||| | |
CHEF GRO:                                TTCCAGCCACCTTCTGCACTCC----AGACTC
                                                  10        20

40        50   M  A  R  A  A  L  S  A  A  P  S  N  P
     GCCAGACCCGCCTGCTGAGCCCCATGGCCCGCGCTGCTCTCTCCGCCGCCCCCAGCAATC
     |||||||||  | |||||||||            ||| |||
     CAGCTACACTCCTGCCCAACGCCATGGCCCCA------------GCCACCCGTTCACTC-
     30        40        50   M  A  P              A  T  R  S  L

R  L  L  R  V  A  L  L  L  L  L  L  V  A  A  G  V  R  R  A  A
     CCCGGCTCCTGCGAGTGGCACTGCTGCTCCTGCTCCTGGTAGCCGCTGGCCGGCGCGCAG
     |||       |||  ||| |||  ||||| |||| ||||  ||| | ||||    ||
     -----CTCCGTGCCCCTCTGCTGTTGCTGCTGCTGCTGGCCACCAGCCGCTTGGCTA
      L  R  A  P  L  L  L  L  L  L  L  L  A  T  S  R  L  A  T
                                                    ^

G  A  S  V  A  T  E  L  R  C  Q  C  L  Q  T  L  Q  G  I  H
     GACGAGCGTCCGTGGCCACTGAACTGCGCTCCCAGTGCTTGCAGACCCTGCAGGGAATTC
     ||||  ||  |  || ||||  || ||||||| |||||| ||||||||| ||  ||  |||
     CAGGGGCTCCTGTTGCCAACGAGCTGCGCTGTCAGTGCCTGCAGACCATGACAGGGGTTC
         G  A  P  V  A  N  E  L  R  C  Q  C  L  Q  T  M  T  G  V  H

P  K  N  I  Q  S  V  N  V  K  S  P  G  P  H  C  A  Q  T  E
     ACCCCAAGAACATCCAAAGTGTGAACGTGAAGTCCCCCGGACCCCACTGCGCCCAAACCG
     |||  ||||||||||   | | || ||| | |||||| |||||||||||| |||||||||
     ACCTCAAGAACATCCAGAGCTTGAAGGTGACACCCCCAGGACCCCACTGCACCCAAACCG
          L  K  N  I  E  S  L  K  V  T  P  P  G  P  H  C  T  Q  T  E

V  I  A  T  L  K  N  G  R  K  A  C  L  N  P  A  S  P  I  V
     AAGTCATAGCCACACTCAAGAATGGGCGGAAAGCTTGCCTCAATCCTGCATCCCCCATAG
     |||||||||||| || ||||||||| || || ||||||| || ||||||  ||||||| |
     AAGTCATAGCCACTCTCAAGAATGGTCAGGAAGCTTGCCTTAACCCTGAAGCCCCCATGG
          V  I  A  T  L  K  N  G  Q  E  A  C  L  N  P  E  A  P  M  V

K  K  I  I  E  K  M  L  N  S  D  K  S  N  .
     TTAAGAAAATCATCGAAAAGATGCTGAACACTGACAAATCCAACTGA       377
     || |||| || || ||||||||||| |  |  ||| ||||  |  |||
     TTCAGAAGATTGTCCAAAAGATGCTAAAGAGCGGAATCCGTAAGTAA       357
          Q  K  I  V  Q  K  M  L  K  S  G  I  R  K  .
```

FIG. 3b

HUMAN GRO  3' UNTRANSLATED MESSENGER RNA:

```
378   CCAGAAGGGAGGAGGAAGCTCACTGGTGGCTGTTCCTGAAGGAGGCCCTG   427
428   CCCTTATAGGAACAGAAGAGGAAAGAGAGACACAGCTGCAGAGGCCACCT   477
478   GGATTGTGCCTAATGTGTTTGAGCATCGCTTAGGAGAAGTCTTCTATTTA   527
528   TTTATTTATTCATTAGTTTTGAAGATTCTATGTTAATATTTTAGGTGTAA   577
578   AATAATTAAGGGTATGATTAACTCTACCTGCACACTGTCCTATTATATTC   627
628   ATTCTTTTTGAAATGTCAACCCCAAGTTAGTTCAATCTGGATTCATATTT   677
678   AATTTGAAGGTAGAATGTTTTCAAATGTTCTCCAGTCATTATGTTAATAT   727
728   TTCTGAGGAGCCTGCAACATGCCAGCCACTGTGATAGAGGCTGGCGGATC   777
778   CAAGCAAATGGCCAATGAGATCATTGTGAAGGCAGGGGAATGTATGTGCA   827
828   CATCTGTTTTGTAACTGTTTAGATGAATGTCAGTTGTTATTTATTGAAAT   877
878   GATTTCACAGTGTGTGGTCAACATTTCTCATGTTGAAACTTTAAGAACTA   927
928   AAATGTTCTAAATATCCCTTGGACATTTTATGTCTTTCTTGTAAGGCATA   1027
978   CTGCCTTGTTTAATGGTAGTTTTACAGTGTTTCTGGCTTAGAACAAAGGG   1050
1028  GCTTAATTATTGATGTTTTCGGA
```

CHEF/16 GRO  3' UNTRANSLATED MESSENGER RNA:

```
358   CAGAAGAAGAAGTAAGATTGCTTTGGTGGCGCATCTGTGATCGCTGACTT   407
408   CTGACAACACTGGCTTAACACATTTTACAGTTTCTTACAAGAACCCTATT   457
458   TATTTATGTATTTATTTATTTCACAAAGCTTGTGTATTTTATTTTTACAT   507
508   TAATATTTAACATTGTGGATGTGTTTTATCAATGGTAGTTCAGTTCTGAT   557
558   TGTTCAGTTTGAAGATGGTAGGCTTAAAATATCTCAGTAAACTAATATTT   607
608   ATTGGGAGACCATTAAGTGTCAACCACTGTAAGAGAAGCATGTGGGGTTG   657
658   GGAAAAAAGCAGAGAGATGAGAGCATATGATCATGTTTGTATTAGGGTGA   707
708   GGGAACGTGTGGGAATCTATGTTTGAATGTTTTGGAAAGAATGTCAGTTA   757
758   TTTATTGAATGTCATTTTTTATATTAATGGTCAACATTGACATGTTGAAG   807
808   TTTCCCTTGGACATTTTATGTCTACTTTGTAGGGCATAGTGCCCTGTTAT   857
858   ATTCTTTAACCAATGTTTCTCTTTGTCTTGTGACAGAGAAGTTCAAAGGA   907
908   CTCTTACAAATGAGATAAAAATAAAAAGTTTTAGCAAAAAAAA...      950
```

FIG. 3c

```
              530         540
HUMAN:    CTATTTATTTATTTATTCATTAGTTT
          ||||||||||||||||  ||  |||
CHEF:     CTATTTATTTATGTATTTATTTATTT
              460         470

870
HUMAN:    GTTATTTATTGAA
          |||||||||||||
CHEF:     GTTATTTATTGAA
              760

940       950       960       970       980
HUMAN:    ATGTTCTAAATATCCCTTGGACATTTTATGTCTTTCTTGTAAGGCATACTGCCTTGT
          |||||  ||  |||||||||||||||||||||||  |||||  ||||| |||| |||
CHEF:     ATGTT-GAAGTTTCCCTTGGACATTTTATGTCTACTTTGTAGGGCATAGTGCCCTGT
              810       820       830       840       850
```

PROMOTION OF MATURATION OF HEMATOPOIETIC PROGENITOR CELLS

BACKGROUND OF THE INVENTION

This work was supported by an Outstanding Investigator Grant, CA 39814, to Dr. Ruth Sager from the United States Government, which has rights in the invention. This invention relates to methods for promoting maturation of hematopoietic precursor cells.

GRO is a polypeptide growth factor encoded by a gene termed gro (Anisowicz et al., Proc. Natl. Acad. Sci. USA 84:7188–7292, 1987; Anisowicz et al. Proc. Natl. Acad. Sci. USA 85:9645–9649, 1988). The amino acid sequence of ma human GRO (i.e., the sequence deduced by Anisowicz et al., 1987, from the gro cDNA sequence, but minus the 34-amino acyl residue leader peptide) is identical to a 73-amino acyl residue-long protein present in the conditioned medium of a human malignant melanoma cell line, and which has been termed melanoma growth stimulation activity, or "MGSA" (Richmond et al., Cancer Research 43:2106–2112, 1983; Richmond et al., EMBO J. 7:2025–2033, 1988). Likewise, a protein secreted by activated neutrophils (neutrophil-activating peptide-3 or NAP-3) has an amino-terminal sequence identical to that of GRO/MGSA, at least up to the 31st residue of each (Schroder et al., J. Exp. Med. 171:1091–1100, 1990). GRO/MGSA acts as a growth factor for melanoma cells, lung carcinoma cells, nevus cells, and some immortalized fibroblast cell lines (Richmond and Thomas, J. Cell Biol. 107:40A #203, 1988).

The gro genes exhibit DNA sequence similarities to a family of genes encoding secretory proteins associated with the inflammatory response. The expression of each gene of this family of genes, including gro, is rapidly induced in susceptible cells by such agents as phorbol esters, interleukin-1, and tumor necrosis factor (TNF), as well as other cytokines and growth factors (Anisowicz et al., 1987; Anisowicz et al., 1988). Members of this family encode proteins which exhibit a high degree of sequence homology, including four cysteine residues present in analogous positions; such proteins include platelet factor 4 (Deuel et al., Proc. Natl. Acad. Sci. USA 74:2256, 1977); platelet basic protein and its cleavage products: β-thromboglobulin (Begg et al., Biochemistry 17:1739, 1978) and connective tissue activity peptide III (CTAP III) (Castor et al., Proc. Natl. Acad. Sci. USA 80:765, 1983); interferon inducible protein 10 (IP10) (Luster et al., Nature 315:672, 1985); macrophage inflammatory protein 2 (MIP-2) (Wolpe et al., Proc. Natl. Sci. USA 86:612, 1989); and neutrophil activating peptide-1/interleukin-8 (NAP-1/IL-8) (Walz et al., Biochem. Biophys. Res. Commun. 149:755, 1987) [also known as NAF (Walz et al.; Lindley et al., Proc. Natl. Acad. Sci. USA 85:9199, 1988), MDNCF (Yoshimura et al., Proc. Natl. Acad. Sci. USA 84:9233, 1987), MONAP (Schroder et al., J. Immunol. 139:3474, 1987), and GCP (Van Damme et al., J. Exp. Med. 167:1364, 1988)]. This latter compound is a neutrophil-specific chemotactic factor (Walz et al.; Lindley et al.; Yoshimura et al.; Schroder et al.; and Van Damme et al.) and cellular activator (Wolpe et al.; Lindley et al.), as well as an inhibitor (at low concentrations) (Gimbrone et al., Science 246:1601, 1989) and activator (at high concentrations) (Carveth et al., Biochem. Biophys. Res. Commun. 162:387, 1989) of neutrophil adhesion to endothelial cells.

Based on what is said to be largely indirect evidence, Anisowicz et al. (1988) suggest that the gro gene may play a role "in a variety of important cellular functions: as a putative [positive]early response gene in cell growth, as a mediator of the IL-1-induced inflammatory response in fibroblasts, and as a negative regulatory factor in epithelial cells."

SUMMARY OF THE INVENTION

In general, the invention features a method for promoting maturation of a hematopoietic precursor cell (preferably a CFU-GEMM cell or a CFU-GM cell) of an animal (e.g., a human), which method includes the step of contacting the cell with a maturation-promoting amount of GRO. In preferred embodiments, the cell is first removed from the animal (e.g., by withdrawing bone marrow from a bone of the animal), and is contacted with GRO in vitro; the cell and/or its descendants are then preferably reinserted into the animal, or alternatively into a second animal (most preferably a human).

Also featured is a method for promoting the maturation of a hematopoietic precursor cell (preferably a CFU-GEMM cell or a CFU-GM cell) within an animal (e.g., a human) by treating the animal with a maturation-promoting amount of GRO. The form of GRO utilized in any method of the invention is preferably a recombinant GRO (i.e., produced by expression of a recombinant DNA molecule encoding GRO), and may, for example, have the amino acid sequence of a mature human GRO, or may be an analog or fragment of a naturally-occurring GRO.

Another method of promoting the maturation of a hematopoietic precursor cell within an animal is to introduce into the animal one or more cells capable of excreting GRO (i.e., secreting or otherwise causing GRO to be exported out of the cell); alternatively, a gene encoding and capable of expressing GRO can be introduced into one or more cells of the animal, to form a cell (herein termed a "transgenic cell") capable of excreting GRO within the animal at a level sufficient to promote maturation of the hematopoietic precursor cell.

The term "hematopoietic cells" herein refers to fully differentiated myeloid cells such as erythrocytes or red blood cells, megakaryocytes, monocytes, granulocytes, and eosinophils, as well as fully differentiated lymphoid cells such as B lymphocytes and T lymphocytes; it also encompasses the various hematopoietic precursor cells from which these differentiated cells develop, such as BFU-E (burst-forming units-erythroid), CFU-E (colony forming unit-erythroid), CFU-Meg (colony forming unit-megakaryocyte), CFU-GM (colony forming unit-granulocyte-monocyte), CFU-Eo (colony forming unit-eosinophil), and CFU-GEMM (colony forming unit-granulocyte-erythrocyte-megakaryocyte-monocyte). The interrelationships among these hematopoietic cells and their positions along the various paths of differentiation are illustrated in FIG. 1. "Maturation" of a hematopoietic precursor cell is used herein to mean the generation of descendents of such precursor cell which are either identical to or more differentiated than such precursor cell, or a mixture of both. For example, a CFU-GEMM would be induced by the method of the invention to generate multiple cells, some of which are CFU-GEMMs and others of which are further along the paths of differentiation, such as CFU-GM, CFU-Eo, and megakaryocytes, or are fully differentiated, end-stage cells such as monocytes/ macrophages, platelets, or granulocytes (e.g., neutrophils, basophils, or eosinophils). A maturation-promoting amount of GRO is that amount of protein which is sufficient to cause maturation of a significant number of hematopoietic precursor cells present in a bone marrow or taken from a bone marrow. For example, out of a population of approximately $10^6$ light-density bone marrow cells (i.e., bone marrow cells which do not pellet in the Ficoll-Hypaque method described below) plated on a semi-solid substrate, at least one hematopoietic precursor cell would be induced by this amount of GRO to proliferate until the cell had formed a colony (a group of cells all of which are descended from a single cell) of at least 8 cells (after 7 days incubation at 37° C.) or at least 40 cells (after 14 days incubation at 37° C.), which cells are identical to or more differentiated than the precursor cell from which they were derived. For in vivo treatment with GRO, a maturation-promoting amount of GRO would be an amount capable of increasing the number of hematopoietic cells in the treated patient.

The ability of a given form or amount of GRO to promote maturation of cells can be measured by any standard procedure. For example, this biological activity can be measured in vitro by measuring the colony-promoting activity of GRO on cells taken from a bone marrow and grown on a semi-solid substrate as described below.

By GRO is meant not only the MGSA protein of Richmond et al. (1983, 1988) and the gro-encoded protein of Anisowicz et al. (1987, 1988), but also any comparably active GRO endogenous to any animal species (particularly mammals or other vertebrate species). Three different human gro cDNAs have been cloned. Anisowicz et al. (1987) identified the first (now termed gro α) from a human bladder carcinoma cell line (T24) cDNA library. An adherent monocyte cDNA library probed with gro α cDNA yielded an 880 bp partial cDNA clone, the sequence of which differed somewhat from that of gro α cDNA; this partial cDNA was used to probe a second cDNA library, producing positively-hybridizing clones representing gro α cDNA and two variants termed gro β and gro γ. Partial sequence analysis of genomic clones obtained by probing a human genomic DNA library with gro α cDNA confirmed that the three forms are derived from related but different genes, all three of which appear to map to the same region of chromosome 4q. The nucleotide sequences and predicted translation sequences of the three cDNAs are compared in FIG. 2.

Genes or cDNAs encoding such alternative naturally-occurring GROs may be identified and cloned using human or other gro cDNA as a hybridization probe, in a manner similar to that employed by Anisowicz et al. (1987). The cDNA sequences and corresponding amino acid sequences for human GRO α and for Chinese hamster GRO, as published by Anisowicz et al. (1987), are set forth in FIG. 3. The term GRO also encompasses any analog or fragment of any naturally-occurring GRO, which analog or fragment is stable in solution and exhibits a maturation-promoting biological activity comparable to that of the naturally-occurring GRO/MGSA of which it is an analog or fragment. It is critical only that the maturation promoting portion of GRO/MGSA be provided. The critical portion of GRO/MGSA can be determined by any of a number of standard techniques. For example, the cDNA or cloned gene encoding GRO may be modified by standard in vitro mutagenesis techniques to cause expression of a GRO analog with amino acid substitutions, additions, and/or deletions of one or more amino acids at one or more locations. The amino acid substitutions may be either conservative or non-conservative, and may be designed, for example, to remove proteolytically sensitive sites from the GRO protein. [By conservative is meant that the substituted amino acyl residue is chemically similar (e.g., acidic, basic, hydrophobic, aromatic) to the residue for which it is substituted: for example, substitution of a valine for a leucine.] Examples of GRO proteins with potentially useful additions would include a GRO with a short peptide added to either terminus, such as a leader peptide to facilitate secretion of the protein out of the cell, or a peptide added by means of genetic engineering to provide an antigenic site to permit immunoaffinity-based purification of the protein product; and chimeric GRO proteins covalently bound to polypeptide ligands capable of binding to particular receptors. Forms of GRO with internal amino acid additions which do not destroy the maturation promoting activity are also within the definition of GRO. Once generated, any such analogs can then be tested for the desired biological activity, i.e. maturation promoting activity. In this way, the maturation promoting portion of GRO can be specifically determined, and those amino acyl residues not critical to that function removed or replaced with other residues. Alternatively, the naturally-occurring or recombinant protein may be digested with a variety of proteases, for example, trypsin, to provide fragments which can then be tested for maturation promoting activity. Those fragments or analogs which have the maturation promoting portion of naturally-occurring GRO can be readily determined using simple in vitro techniques.

Also included by the term GRO is a protein or polypeptide having an amino acid sequence of between 70 and 100 amino acyl residues with either (a) a contiguous 20-residue segment thereof having at least 80% sequence homology with a portion of a naturally-occurring mature GRO (i.e., when the 20-residue segment is lined up with such portion of a naturally-occurring mature GRO, at least 80% of the residues of the former will be identical to the corresponding residues of the latter), or (b) a contiguous 10-residue segment thereof having at least 90% sequence homology with a portion of a naturally-occurring mature GRO. If the GRO polypeptide is of lesser size than 70 amino acids (for example 20 to 30 amino acids), such polypeptide will have at least 80% sequence homology with some portion of the naturally-occurring GRO. GRO can be produced by any standard technique, including by extraction from animal tissues or cells which naturally produce the protein or can be induced to do so, by chemical synthesis, and by recombinant DNA technology. As discussed above, the DNA encoding the desired GRO can be modified by standard techniques to encode a GRO having a different amino acid sequence from that described by Richmond et al., 1988, and Anisowicz et al., 1987, and may be expressed in any desired cell type. It is not necessary that GRO be produced in a glycosylated state, since the naturally-occurring protein is not glycosylated.

Applicants have surprisingly discovered that GRO is useful for promoting maturation of certain hematopoietic precursor cells. Previously, factors which were useful for promoting hematopoietic precursor cell maturation included colony-stimulating factors (CSFs) such as multi-CSF (also termed interleukin-3 or IL-3), granulocyte colony stimulating factor (G-CSF), macrophage colony stimulating factor (M-CSF), and granulocyte-macrophage colony stimulating factor (GM-CSF). All of these are glycoproteins of molecular weight 14-45 kD that are synthesized by multiple cell types including endothelial cells, fibroblasts, macrophages, and lymphocytes. In contrast, GRO is not a glycosylated protein and has a molecular weight of only 7 kD. Further, its amino acid sequence is very different from the respective sequences of the known CSFs. Other factors which have been found to work in synergy with the CSFs include IL-1 and IL-6, neither of which has an amino acid sequence similar to that of GRO.

The method of the invention provides a way to boost a patient's level of fully differentiated hematopoietic cells (such as granulocytes and macrophages) by inducing the proliferation and maturation of hematopoietic precursor cells. Therapy with GRO can be accomplished either in vivo or ex vivo, and can utilize the patient's own bone marrow cells or cells provided by a donor. GRO may be used alone or in combination with other growth factors/cytokines such as the interleukins (particularly IL-1, IL-3, IL-6, and IL-8), the colony stimulating factors (e.g., GM-CSF, G-CSF, and M-CSF), and erythropoietin, in order to achieve optimal clinical results.

Other features and advantages of the invention will be apparent from the following description of the preferred embodiments thereof, and from the claims.

DESCRIPTION OF THE PREFERRED EMBODIMENTS

The drawings are first briefly described.

Figures 2A, 2B:
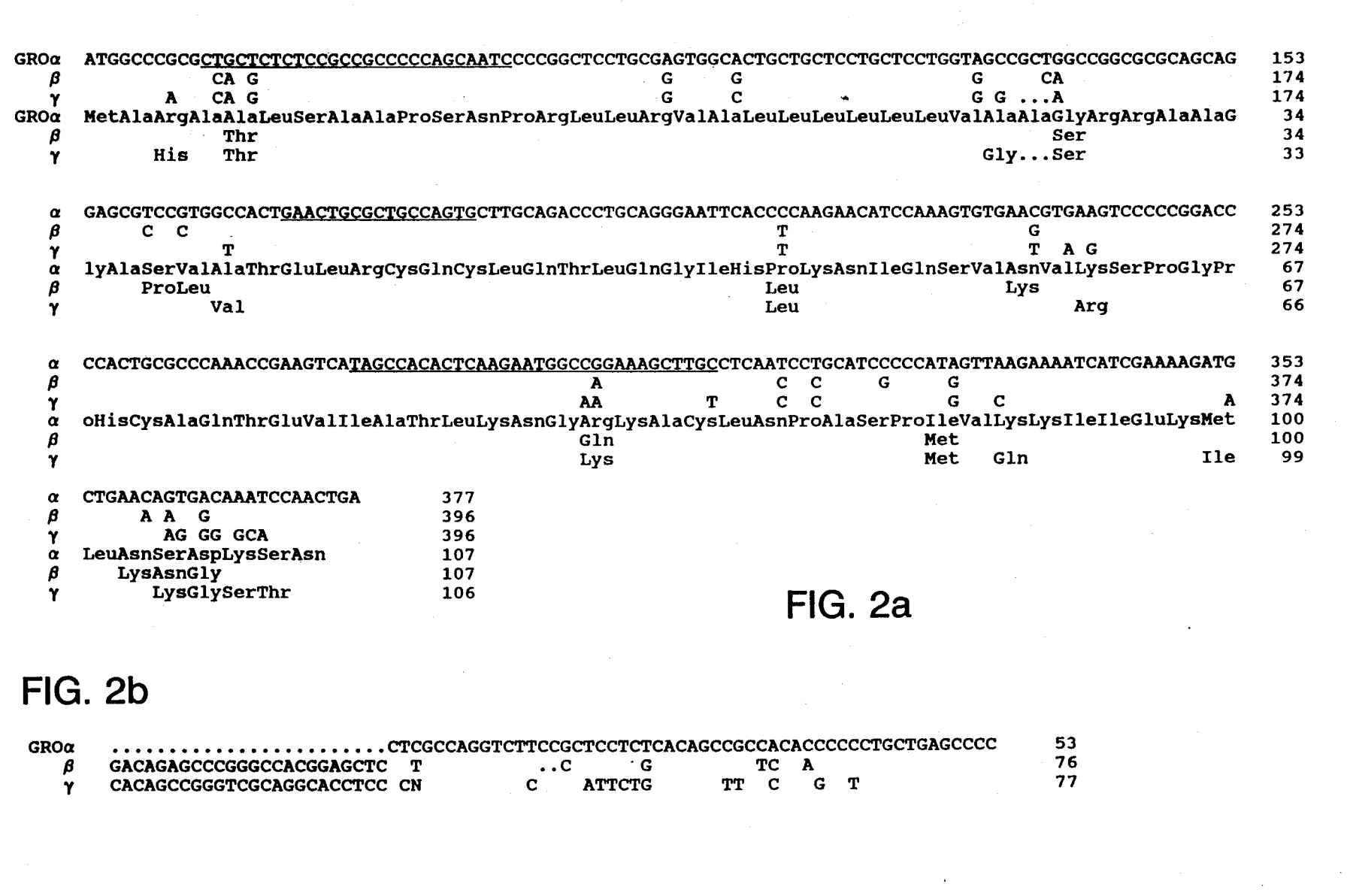

FIG. 2 is a comparative representation of the cDNA sequences of human gro α, gro β, and gro γ: (A) the coding sequences, with corresponding amino acid sequences; (B) the 5' untranslated sequences; and (C) the 3' untranslated sequences, with a conserved region shown boxed.

FIG. 3 is a representation of the nucleotide sequences and corresponding amino acid sequences for human GRO α and Chinese hamster GRO: (A) 5' untranslated and protein coding regions. (B) 3' untranslated regions. (C) regions of significant homology between the human and the Chinese hamster gro cDNA 3' untranslated regions. (Taken from FIGS. 4 and 5 of Anisowicz et al., 1987.)

PREPARATION OF GRO

Figure 1:
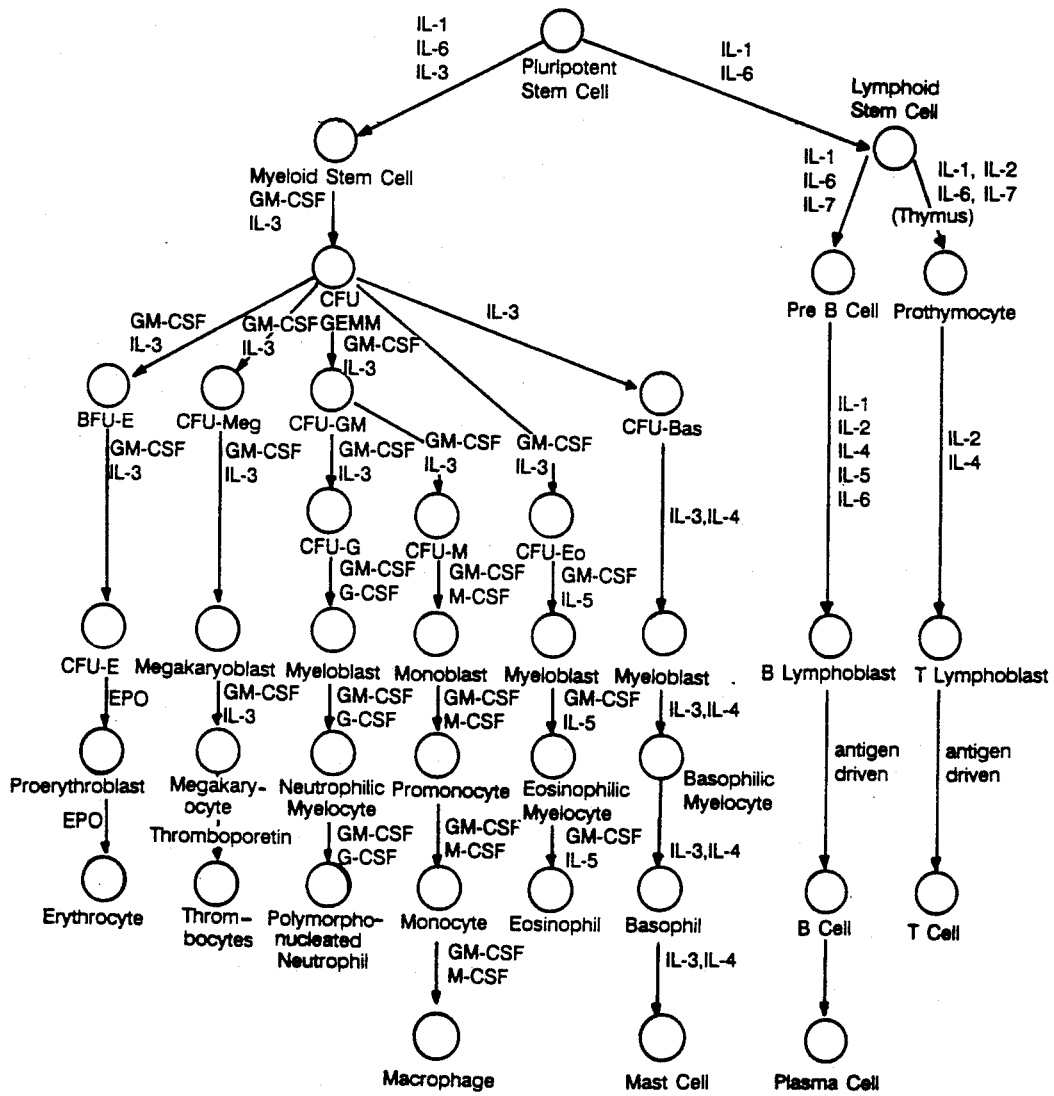
FIG. 1 is a diagram illustrating the interrelated paths of differentiation of various hematopoietic cells. (taken from a 1990 illustration produced by Schering Plough Corporation and Sandoz Pharmaceuticals Corporation).

As stated above, GRO may be prepared by any standard 10 method, including but not limited to those utilizing recombinant DNA techniques. Two independent preparative methods are described below in Examples 1 and 2, but alternative methods will be apparent to those of ordinary skill in the art of protein production.

EXAMPLE 1

COS-1 cells (ATCC No.CRL1650) were transiently transfected with a pXM expression vector (available from Genetics Institute, Cambridge, Mass.) containing human gro cDNA (Anisowicz et al., 1987). Cells were maintained for one day in Alpha medium (Gibco) containing 10% fetal calf serum (FCS), and then were washed with serum-free medium and maintained for two days in Alpha salts plus 100 U/ml penicillin and 100 μg/ml streptomycin. Culture medium was harvested and subjected to low-speed centrifugation (500 × g for 5 min) to pellet cellular debris. The culture supernatant was dialyzed against 10 mM sodium phosphate, pH 6.5, and applied directly to a cation exchange column (CM-Sephadex, Pharmacia, Uppsala, Sweden). The bound proteins were eluted with a linear salt gradient of 0 to 0.7 M NaCl in 10 mM sodium phosphate, pH 6.5. GRO-containing fractions were determined by analyzing aliquots of each fraction on 18% SDS-polyacrylamide gels, with a distinct silver-staining band at 6 kD indicative of the presence of mature recombinant GRO. The identity of the GRO-containing band was confirmed by positive cross-reactivity with an antibody prepared against a 10-amino acyl residue carboxy-terminal fragment of GRO. GRO-containing fractions were pooled and the protein was concentrated by differential filtration through a membrane with a molecular weight cut-off of 3,000 daltons.

EXAMPLE 2

An analog of mature human GRO [differing from naturally-occurring mature human GRO α by an amino-terminal octapeptide tag: AspTyrLysAspAspAspAspLys (Hopp et al., Biotechnology 6:1204–1210, 1988)] was produced in yeast by recombinant DNA techniques. A segment of gro cDNA encoding mature human GRO α was inserted into the yeast expression plasmid paADH2 (Price et al., Gene 55:287–293, 1987) and expressed in S. cerevisiae strain XV218/(a/α-trp-1). The resulting GRO analog was purified in a one-step immunoaffinity procedure utilizing an antibody specific for the first four residues of the octapeptide tag, according to the method of Hopp et al.

Biolooical Assays for GRO

GRO (including fragments and analogs of a naturally-occurring GRO) may be assayed for biological activity by a method such as one described in Examples 3–5.

EXAMPLE 3:

Assay for Maturation Promotion Activity

The ability of GRO to promote maturation of hematopoietic precursor cells can be conveniently assayed in vitro by an assay such as the one herein described. Functional variations on this assay, and alternative assays, will be apparent to those of ordinary skill in the art.

Bone marrow from a normal human or other animal is harvested by standard sterile procedures, heparinized, and either frozen or used immediately. Light-density bone marrow cells are isolated by density gradient centrifugation on Ficoll-Hypaque (LSM, Organon Technica, Durham, N.C.) according to standard methods, and then washed and adjusted to $1 \times 10^6$ cell/ml in RPMI 1640 medium (Gibco) containing 100 U/ml penicillin, 100 μg/ml streptomycin, 12.5% FCS, and 12.5% horse serum. The cells ($1 \times 10^5$) are plated in duplicate on Lux 35-mm gridded culture dishes (Nunc, Inc., Naperville, Ill.) in 1.0 ml of the same culture medium containing methylcellulose (1500 centipoise) at a final concentration of 0.9% (w/v). The GRO preparation to be tested is added to a final concentration of, for example, 25, 50, or 100 ng/ml. The dishes are then placed in a 150 mm dish with water for humidification, and incubated in 5% $CO_2$ in air at 37° C. After 14 days of incubation, plates are scored for hematopoietic cell colonies ($\geq$ 40 cells/aggregate). Each colony generally contains a mixture of hematopoietic cell types, with the particular combination of types present in a given colony indicative of the identity of the hematopoietic precursor cell from which the colony descended. For example, a colony which contains only granulocytes, monocytes, and/or CFU-GM cells arises by the action of a maturation-promoting activity on a single CFU-GM cell and would be scored as a CFU-GM colony, while a second colony which contains those three cell types plus eosinophils, CFU-Eo, megakaryocytes, erythrocytes, CFU-Meg, CFU-E, BFU-E, and/or CFU-GEMM is descended from a more primitive precursor cell, a CFU-GEMM, and so would be scored as a CFU-GEMM colony. Methods of distinguishing one hematopoietic cell type from another are well known to those of ordinary skill in the field of hematology. For example, the cellular morphology of individual colonies may be evaluated by differential counts performed on cytocentrifuge preparations of cells stained with the Diff-Quick modification (Sigma Chemical Co., St. Louis, Mo.) of the Wright's Giemsa technique.

As a negative control, an equivalent aliquot of buffer lacking GRO (or any cytokine) is added to similarly prepared bone marrow cells. Positive controls vary with the specific type of hematopoietic precursor cell being analyzed for colony formation. In the experiments set forth in Table I below, recombinant human GM-CSF at 5 U/ml (Genetics Institute, Cambridge, Mass.) was used as a positive control for induction of colony formation by CFU-GM cells, while a combination of 2 U/ml recombinant human erythropoietin (Amgen, Thousand Oaks, Calif.), 0.5 mM 2-mercaptoethanol, and conditioned culture medium from the human bladder carcinoma cell line 5637 (Welte et al., Proc. Natl. Acad. Sci. USA 82:1526, 1985) was used as a positive control for induction of colony formation by both CFU-GEMM and burst forming unit-erythroid (BFU-E) cells. The choice of other cytokines as positive controls for induction of formation of colonies by other types of hematopoietic cells is within the skills of those in the field to which the invention pertains.

The results of six separate experiments using the above-described in vitro assay to test the bioactivity of recombinant human GRO α are shown in Table I below. The number of colonies formed after incubation for 14 days in the presence of each concentration of GRO tested (100 ng/ml, 50 ng/ml and 25 ng/ml) is expressed as a percentage of the colonies formed after incubation for a similar period in the presence of the applicable positive control cytokine (as described above). Under these culture conditions, the positive controls generate approximately 100-250 CFU-GM colonies, 24-60 CFU-GEMM colonies, and 40 ∝ 200 BFU-E colonies per $10^6$ bone marrow cells plated. Values for negative control plates are shown immediately below each corresponding GRO test result. The results show that recombinant human GRO is capable of stimulating generation of colonies of CFU-GM cells, CFU-GEMM cells, and possibly BFU-E cells in a bone marrow cell preparation, in some cases to a extent greater than that seen in the positive control.

TABLE I

COLONY FORMATION BY BONE MARROW CELLS TREATED WITH GRO

Number of colonies/$10^6$ light-density bone marrow cells expressed as a % of (+)control

| | CFU-GM | CFU-GEMM | BFU-E |
|---|---|---|---|
| Experiment #1 | | | |
| GRO (100 ng/ml) | 87% | 103% | 70% |
| Buffer (1:15) | 76 | 32 | 34 |
| GRO (50 ng/ml) | 98 | 64.5 | 64 |
| Buffer (1:30) | 67 | 26 | 27 |
| GRO (25 ng/ml) | 76 | 48.4 | 56 |
| Buffer (1:60) | 70 | 16 | 15 |
| Experiment #2 | | | |
| GRO (100 ng/ml) | 69 | 82 | 82 |
| Buffer (1:15) | 35 | 35 | 64 |
| GRO (50 ng/ml) | ND | ND | ND |
| Buffer (1:30) | 18 | 41 | 9 |
| GRO (25 ng/ml) | 102 | 88 | 86 |
| Buffer (1:60) | 18 | 24 | 18 |
| Experiment #3 | | | |
| GRO (100 ng/ml) | 117 | 116 | 99 |
| Buffer (1:15) | 69 | 37 | 84 |
| GRO (50 ng/ml) | 172 | 130 | 74 |
| Buffer (1:30) | 74 | 63 | 63 |
| GRO (25 ng/ml) | 109 | 137 | 93 |
| Buffer (1:60) | 87 | 87 | 28 |
| Experiment #4 | | | |
| GRO (100 ng/ml) | 115% | 125% | 65% |
| Buffer (1:15) | 38 | 25 | 10 |
| GRO (50 ng/ml) | 91 | 108 | 45 |
| Buffer (1:30) | 35 | 17 | 15 |
| GRO (25 ng/ml) | 62 | 75 | 15 |
| Buffer (1:60) | 29 | 33 | 10 |
| Experiment #5 | | | |
| GRO (100 ng/ml) | 72 | 68 | 9 |
| Buffer (1:15) | 58 | 19 | 5 |
| GRO (50 ng/ml) | 66 | 50 | 14 |
| Buffer (1:30) | 38 | 19 | 2 |
| GRO (25 ng/ml) | 57 | 69 | 5 |
| Buffer (1:60) | 35 | 31 | 2 |
| Experiment #6 | | | |
| GRO (100 ng/ml) | 75 | 7 | 40 |
| Buffer (1:15) | 14 | 0 | 5 |
| GRO (50 ng/ml) | 83 | 4 | 15 |
| Buffer (1:30) | 18 | 1 | 0 |
| GRO (25 ng/ml) | 98 | 12 | 25 |
| Buffer (1:60) | 7 | 1 | 0 |

EXAMPLE 4:

Assay Following Depletion of Accessory Cells

In order to determine whether or not GRO stimulates proliferation by direct action on the proliferating cells, or by inducing production of an undetermined cytokine by other "accessory" cells present in the bone marrow preparation, an accessory cell depletion experiment was carried out. Light-density bone marrow cells were prepared as described above and depleted of monocytes by exposing the preparation to a plastic Petri dish for 3 hours to permit adherence of monocytes. Non-adherent cells were then removed from the dish, washed, and subjected to further analysis. Depletion of NK (natural killer) and T lymphocytes was accomplished by E rosetting by the method of Elliott and Pross (Methods in Enzymology 108:49-64, 1984). The results of treating such depleted bone marrow cell populations with recombinant GRO, shown in Table II, indicate that GRO retains most or all of its ability to stimulate maturation of CFU-GM cells even in the absence of monocytes and/or NK and T cells, suggesting that GRO may act directly on the proliferating CFU-GM cells. In contrast, the ability of GRO to stimulate formation of colonies by CFU-GEMM appears to be decreased in the absence of such accessory cells. This result suggests that GRO affects CFU-GEMM cells at least in part by an indirect route that involves other cells, perhaps by inducing accessory cells to produce a different growth-stimulating cytokine.

TABLE II

COLONY FORMATION BY ACCESSORY CELL-DEPLETED BONE MARROW CELLS TREATED WITH GRO

| | Number of colonies/$10^6$ (pre-depletion) bone marrow cells, expressed as a % of (+)control | | |
|---|---|---|---|
| | CFU-GM | CFU-GEMM | BFU-E |
| Experiment #7 | | | |
| *Monocyte-depleted* | | | |
| GRO (100 ng/ml) | 121% | 18% | 16% |
| GRO (50 ng/ml) | 80 | 11 | 16 |
| GRO (25 ng/ml) | 78 | 46 | 8 |
| (−)control (buffer) | 26 | 7 | 0 |
| *NK + T cell-depleted* | | | |
| GRO (100 ng/ml) | 93 | 79 | 20 |
| GRO (50 ng/ml) | 93 | 114 | 17 |
| GRO (25 ng/ml) | 101 | 129 | 34 |
| (−)control (buffer) | 31 | 7 | 2 |
| Experiment #8 | | | |
| *Monocyte-depleted* | | | |
| GRO (100 ng/ml) | 128 | 41 | 40 |
| GRO (50 ng/ml) | 124 | 72 | 27 |
| GRO (25 ng/ml) | 131 | 45 | 19 |
| (−)control (buffer) | 56 | 24 | 6 |
| *NK + T cell-depleted* | | | |
| GRO (100 ng/ml) | 115 | 71 | 38 |
| GRO (50 ng/ml) | 142 | 71 | 23 |
| GRO (25 ng/ml) | 104 | 150 | 54 |
| (−)control (buffer) | 51 | 21 | 0 |
| Experiment #9 | | | |
| *NK + T cell-depleted* | | | |
| GRO (100 ng/ml) | 112% | 400% | 13% |
| GRO (50 ng/ml) | 75 | 300 | 17 |
| GRO (25 ng/ml) | 46 | 400 | 20 |
| (−)control (buffer) | 31 | 0 | 0 |
| *Monocyte + NK + T cell-depleted* | | | |
| GRO (100 ng/ml) | 82 | 100 | 5 |
| GRO (50 ng/ml) | 71 | 250 | 5 |
| GRO (25 ng/ml) | 87 | 100 | 5 |
| (−)control (buffer) | 23 | 0 | 5 |
| Experiment #10 | | | |
| *NK + T cell-depleted* | | | |
| GRO (100 ng/ml) | 89 | 0 | 0 |
| GRO (50 ng/ml) | 83 | 0 | 0 |
| GRO (25 ng/ml) | 58 | 0 | 0 |
| (−)control (buffer) | 20 | 0 | 0 |
| *Monocyte + NK + T cell-depleted* | | | |
| GRO (100 ng/ml) | 58 | 11 | 3 |
| GRO (50 ng/ml) | 26 | 11 | 3 |
| GRO (25 ng/ml) | 26 | 0 | 0 |
| (−)control (buffer) | 9 | 0 | 0 |

EXAMPLE 5:

Chemotaxis Assay

Figure 4:
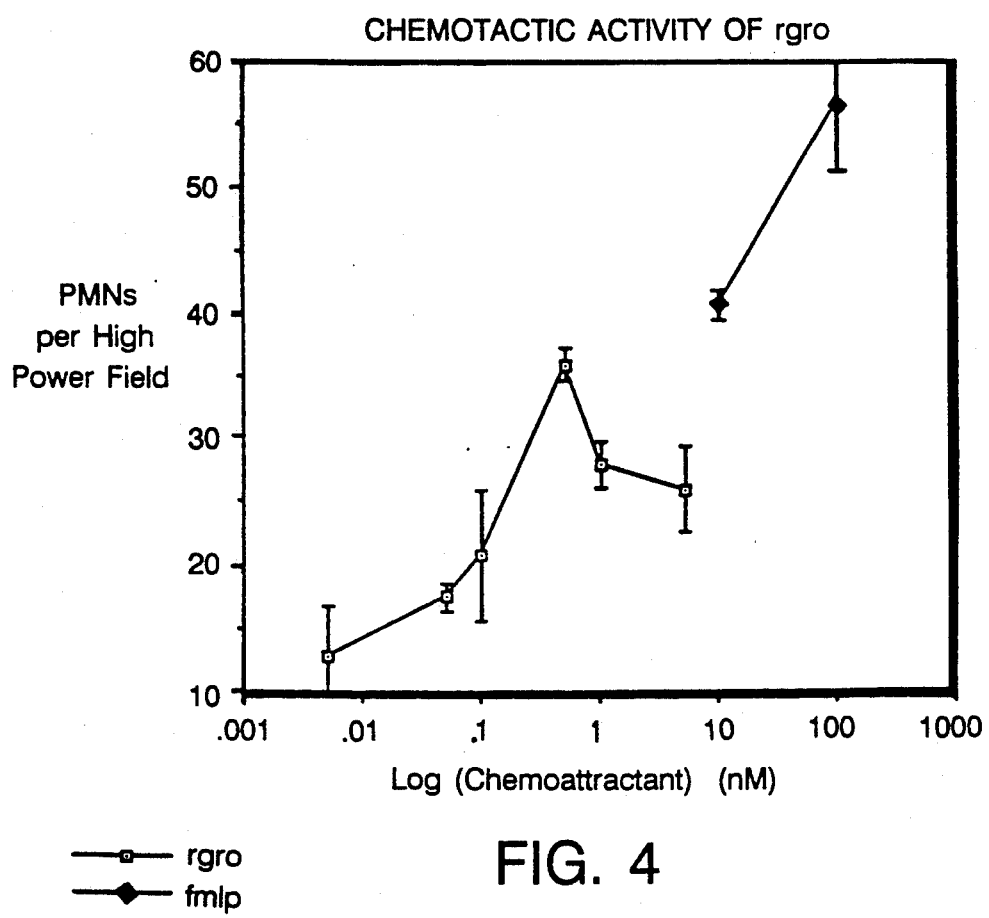
FIG. 4 is a graph showing the chemotactic activity of recombinant GRO (rgro) and a known chemoattractant, f-Met-Leu-Phe (fmlp), for polymorphonuclear leukocytes (PMNs).

Certain members of the gene family to which the gro genes are related encode proteins which are chemotactic for neutrophils. In order to determine whether or not recombinant GRO is also chemotactic for such cells, the following assay was carried out:

Human peripheral venous blood taken from normal volunteers was subjected to dextran sedimentation (Pharmacia, Uppsala, Sweden) followed by centrifugation on Ficoll-Hypaque (Lympho-prep, Organon Technica, Durham, N.C.) as described by Williams et al. (Proc. Natl. Acad. Sci. USA 74:1204, 1977). Pellets containing polymorphonuclear leukocytes (PMNs, a type of neutrophil) were subjected to hypotonic lysis (x2); they contained greater than 95% PMNs as judged by microscopic examination of Wright's stained specimens. The buffy coat containing mononuclear cells was washed twice with Hank's balanced salt solution (Gibco, Grand Island, N.Y.) containing 0.01 M HEPES, pH 7.0; 4.3 mM $NaHCO_3$ (HBSS) and 2% bovine serum albumin (HBSS-BSA). Mononuclear cell preparations contained 25–35% monocytes as determined by nonspecific esterase staining. Chemotaxis was quantified using 48-well microchambers (Neuroprobe, Inc., Cabin John, MD) (Harvath et al., J. Immunol. Methods 37:39, 1980; Falk et al., J. Immunol. Methods 33:239, 1980). PMNs (0.05 ml, 1 × $10^6$/ml) suspended in HBSS, pH 7.2, were placed in the upper wells of the microchamber. HBSS alone or HBSS containing GRO or another chemotactic stimulant (0.03 ml) was placed in each of the lower chambers and was separated from the cells by a 3.0 μm pore diameter polyvinyl pyrrolidine (PVP)-free polycarbonate filter (25 mm × 80 mm). Following incubation at 37° C. in humidified air for 60 min, the non-migrated cells were removed from the top of the filter, as counted and the migrated cells were stained with a leukocyte-specific stain (Leuko Stat, Fisher Scientific, Orangeberg, N.Y.). PMN chemotaxis was quantified as the average number of cells/field which had migrated completely through the filter, as counted in ten oil immersion (x 1000) fields. Assays were performed in triplicate and expressed as the mean cells/field ± S.D. As shown in FIG. 4, recombinant human GRO increased the number of migrated PMNs approximately 2.8-fold when compared to HBSS alone. GRO induced significant migration of PMNs in concentrations ranging from 0.05 nM to 5.0 nM. Maximal neutrophil chemotactic activity was obtained at a GRO concentration of 0.7 ± 0.2 nM, with an effective concentration which produced 50% of maximal migration ($EC_{50}$) of 0.07 ± 0.05 nM. The total number of cells migrating in response to GRO ranged from 53% to 83% of the number of cells responding to 100 nM f-Met-Leu-Phe, a known chemoattractant. Monocyte chemotaxis was similarly quantified in the 48-well microchambers except that cells were suspended to 1.5 × $10^6$ monocytes/ml in HBSS-BSA, pH 7.0; 5.0 μm PVP-coated polycarbonate filters were used; and incubations were allowed to proceed for 90 min in 37° C. humidified air. Unlike human PMNs, human monocytes did not respond chemotactically to concentrations of GRO ranging from 0.01 nM to 10 nM (data not shown).

These results, analogous to those produced by NAP-3 and NAP-1/IL-8, suggest a role for GRO in acute inflammation.

Use

The maturation promoting ability of GRO is useful for treatment of a variety of diseases and conditions. For example, it can be used to promote regeneration of hematopoietic cells between cycles of myelotoxic chemotherapy, permitting use of increased doses of chemotherapeutic agents. The protein may also be used during or after autologous, allogeneic, or even xenogeneic bone marrow transplantation to promote accelerated engraftment. In addition, a number of genetic diseases characterized by neutropenia and thrombocytopenia can be treated by promoting the maturation of appropriate hematopoietic precursor cells. Continuous low-dose therapy will result in an increase in the patient's level of durable neutrophils and platelets. Azidothymidine (AZT) treatment of acquired immunodeficiency syndrome (AIDS) patients can induce severe neutropenia and anemia, which can be combatted by GRO therapy. Thus, GRO is broadly useful for treatment of hematopoietic cell deficiencies, whether congenital or therapy-induced.

GRO therapy can be accomplished by treating the patient systemically with an intravenous bolus or infusion of GRO (e.g. 1-100 µg/kg body weight per day) in a pharmaceutically effective carrier, or by any other effective means (such as an oral dose of a GRO analog that retains its potency when so administered, or by localizing the GRO injection directly to the in vivo site of the bone marrow to be treated). Alternatively, a preparation of the patient's bone marrow (or the bone marrow of a donor) can be treated ex vivo with GRO, cultured for a period to permit generation of hematopoietic cells, and then implanted in the patient.

Other embodiments are within the following claims.

What is claimed is:

1. A method for promoting maturation of a hematopoietic precursor cell of an animal, said method comprising
   removing said cell from said animal, and
   contacting said cell with a maturation-promoting amount of a polypeptide comprising a naturally-occurring GRO.

2. The method of claim 1, wherein said cell is reinserted into said animal after contacting said cell with said GRO.

3. The method of claim 1, wherein a progeny of said cell is inserted into said animal after contacting said cell with said GRO.

4. The method of claim 1, wherein said cell is inserted into a second animal after contacting said cell with said GRO.

5. The method of claim 1, wherein a progeny of said cell is inserted into a second animal after contacting said cell with said GRO.

6. The method of claim 4 or claim 5, wherein said second animal is a human.

7. The method of claim 1, 2, 3, 4, or 5, wherein said animal is a human.

8. The method of claim 1 wherein said GRO is a mature human GRO.

9. The method of claim 1, wherein said GRO is a recombinant GRO.

10. The method of claim 1, wherein said cell is selected from a CFU-GEMM cell and a CFU-GM cell.

11. The method of claim 1, wherein said GRO is human GRO α.

12. The method of claim 1, wherein said GRO is human GRO β.

13. The method of claim 1, wherein said GRO is human GRO γ.

* * * * *

UNITED STATES PATENT AND TRADEMARK OFFICE
CERTIFICATE OF CORRECTION

PATENT NO.   : 5,154,921
DATED        : October 13, 1992
INVENTOR(S)  : Ruth Sager, et al It is certified that error appears in the above-indentified patent and that said Letters Patent is hereby corrected as shown below:

On title page, item [56] References Cited, under "Other Publications", (fourth publication) "issue" should be --issued--

Col. 1, line 13, "7292" should be --7192--.
Col. 1, line 15; "ma" should be --mature--.
Col. 5, line 64; delete "10".
Col. 7, line 63; "40 α 200" should be --40-200--.
Col. 8, line 2; "a" should be --an--.

Signed and Sealed this

Twelfth Day of April, 1994

Attest:

BRUCE LEHMAN

*Attesting Officer*          *Commissioner of Patents and Trademarks*

UNITED STATES PATENT AND TRADEMARK OFFICE
CERTIFICATE OF CORRECTION

PATENT NO. : 5,154,921

DATED : October 13, 1992

INVENTOR(S) : Ruth Sager, Douglas Trask, and Phong Le

It is certified that error appears in the above-indentified patent and that said Letters Patent is hereby corrected as shown below:

On the title page, item [73], following Dana-Farber Cancer Institute, Inc., Boston, Mass. insert --Duke University, Durham, North Carolina.--.

Signed and Sealed this

Thirty-first Day of May, 1994

Attest:

BRUCE LEHMAN

Attesting Officer     Commissioner of Patents and Trademarks